US009061033B2

(12) United States Patent (10) Patent No.: US 9,061,033 B2
Fallon (45) Date of Patent: Jun. 23, 2015

(54) METHODS AND COMPOSITIONS FOR THE TREATMENT OF SYMPTOMS OF PRION DISEASES

(71) Applicant: CUREMARK LLC, Rye, NY (US)

(72) Inventor: Joan M. Fallon, Bronxville, NY (US)

(73) Assignee: CUREMARK LLC, Rye, NY (US)

(*) Notice: Subject to any disclaimer, the term of this patent is extended or adjusted under 35 U.S.C. 154(b) by 0 days.

(21) Appl. No.: 13/737,225

(22) Filed: Jan. 9, 2013

(65) Prior Publication Data

US 2013/0195833 A1 Aug. 1, 2013

Related U.S. Application Data

(63) Continuation of application No. 12/573,353, filed on Oct. 5, 2009, now abandoned.

(60) Provisional application No. 61/102,818, filed on Oct. 3, 2008.

(51) Int. Cl.
    *A61K 38/54* (2006.01)
    *A61K 38/47* (2006.01)
    *C12Q 1/37* (2006.01)
    *G01N 33/68* (2006.01)
    *A61K 38/46* (2006.01)
    *A61K 38/48* (2006.01)
    *A61K 36/185* (2006.01)

(52) U.S. Cl.
    CPC .............. *A61K 38/54* (2013.01); *A61K 38/47* (2013.01); *C12Q 1/37* (2013.01); *G01N 33/6896* (2013.01); *G01N 2333/976* (2013.01); *G01N 2800/2828* (2013.01); *A61K 38/465* (2013.01); *A61K 38/4826* (2013.01); *A61K 38/4873* (2013.01); *A61K 36/185* (2013.01)

(58) Field of Classification Search
    None
    See application file for complete search history.

(56) References Cited

U.S. PATENT DOCUMENTS

| | | | |
|---|---|---|---|
| 3,002,883 A | 10/1961 | Butt et al. |
| 3,223,594 A | 12/1965 | Serge |
| 3,322,626 A | 5/1967 | D'Argento |
| 3,357,894 A | 12/1967 | Jose et al. |
| 3,515,642 A | 6/1970 | Mima et al. |
| 3,574,819 A | 4/1971 | Gross et al. |
| 3,860,708 A | 1/1975 | Prout |
| 3,940,478 A | 2/1976 | Kurtz |
| 4,079,125 A | 3/1978 | Sipos |
| 4,145,410 A | 3/1979 | Sears |
| 4,241,046 A | 12/1980 | Papahadjopoulos et al. |
| 4,280,971 A | 7/1981 | Wischniewski et al. |
| 4,447,412 A | 5/1984 | Bilton |
| 4,456,544 A | 6/1984 | Lupova et al. |
| 4,623,624 A | 11/1986 | Schultze |
| 4,826,679 A | 5/1989 | Roy |
| 5,190,775 A | 3/1993 | Klose |
| 5,250,418 A | 10/1993 | Moller et al. |
| 5,324,514 A | 6/1994 | Sipos |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |
| 5,750,104 A | 5/1998 | Sipos |
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |

(Continued)

FOREIGN PATENT DOCUMENTS

| | | |
|---|---|---|
| CA | 2198317 A1 | 2/1997 |
| CA | 2263703 A1 | 8/1999 |

(Continued)

OTHER PUBLICATIONS

Sundstrom et al., J. Neurosci. Nurs., 2003, vol. 35, No. 6, p. 300-305, Abstract Only.*

(Continued)

*Primary Examiner* — Kade Ariani

(74) *Attorney, Agent, or Firm* — Wilson Sonsini Goodrich & Rosati, P.C.

(57) ABSTRACT

A therapeutic composition for the treatment of the symptoms of prion diseases and the method for preparing the therapeutic agents is disclosed. The therapeutic composition is a stable pharmaceutical composition comprising one or more digestive and/or pancreatic enzymes. The therapeutic composition may be manufactured by a variety of encapsulation technologies. Delivery of the therapeutic composition may be made orally, through injection, by adherence of a medicated patch or other method. Further, a method of using fecal chymotrypsin level as a biomarker for the presence of a prion disease, or the likelihood of an individual to develop a prion disease is disclosed.

15 Claims, No Drawings

(56) References Cited

U.S. PATENT DOCUMENTS

| | | | |
|---|---|---|---|
| 6,096,338 A | 8/2000 | Lacy et al. | |
| 6,149,585 A | 11/2000 | Gray | |
| 6,153,236 A | 11/2000 | Wu et al. | |
| 6,168,569 B1 | 1/2001 | McEwen et al. | |
| 6,187,309 B1 | 2/2001 | McMichael et al. | |
| 6,197,746 B1 | 3/2001 | Beck et al. | |
| 6,210,950 B1 | 4/2001 | Johnson et al. | |
| 6,251,478 B1 | 6/2001 | Pacifico et al. | |
| 6,261,602 B1 | 7/2001 | Calanchi et al. | |
| 6,261,613 B1 | 7/2001 | Narayanaswamy et al. | |
| 6,280,726 B1 | 8/2001 | Weinrauch et al. | |
| 6,287,585 B1 | 9/2001 | Johansen | |
| 6,309,669 B1 | 10/2001 | Setterstrom et al. | |
| 6,399,101 B1 | 6/2002 | Frontanes et al. | |
| 6,482,839 B1 | 11/2002 | Thornfeldt | |
| 6,498,143 B1 | 12/2002 | Beck et al. | |
| 6,534,063 B1 | 3/2003 | Fallon | |
| 6,534,259 B1 | 3/2003 | Wakefield | |
| 6,558,708 B1 | 5/2003 | Lin | |
| 6,562,629 B1 | 5/2003 | Lin et al. | |
| 6,569,463 B2 | 5/2003 | Patel et al. | |
| 6,632,429 B1 | 10/2003 | Fallon | |
| 6,660,831 B2 | 12/2003 | Fallon | |
| 6,727,073 B1 | 4/2004 | Moore et al. | |
| 6,743,447 B2 | 6/2004 | Labergerie et al. | |
| 6,764,447 B2 | 7/2004 | Iliff | |
| 6,783,757 B2 | 8/2004 | Brudnak | |
| 6,790,825 B2 | 9/2004 | Beck et al. | |
| 6,797,291 B2 | 9/2004 | Richardson | |
| 6,808,708 B2 | 10/2004 | Houston | |
| 6,821,514 B2 | 11/2004 | Houston | |
| 6,827,688 B2 | 12/2004 | Goto et al. | |
| 6,835,397 B2 | 12/2004 | Lee et al. | |
| 6,852,487 B1 | 2/2005 | Barany et al. | |
| 6,861,053 B1 | 3/2005 | Lin et al. | |
| 6,899,876 B2 | 5/2005 | Houston | |
| 6,923,988 B2 | 8/2005 | Patel et al. | |
| 6,980,958 B1 | 12/2005 | Surwit et al. | |
| 7,048,906 B2 | 5/2006 | Lin et al. | |
| 7,081,239 B2 | 7/2006 | Lin | |
| 7,091,182 B2 | 8/2006 | Beck et al. | |
| 7,101,573 B2 | 9/2006 | Szymczak et al. | |
| 7,122,357 B2 | 10/2006 | Sander et al. | |
| 7,129,053 B1 | 10/2006 | Reiter et al. | |
| 7,138,123 B2 | 11/2006 | Fallon | |
| 7,232,670 B2 | 6/2007 | D'Azzo et al. | |
| 7,244,412 B2 | 7/2007 | Lin | |
| 7,285,633 B2 | 10/2007 | Wu et al. | |
| 7,381,698 B2 | 6/2008 | Fein et al. | |
| 7,395,216 B2 | 7/2008 | Rosenfeld et al. | |
| 7,479,378 B2 | 1/2009 | Potthoff et al. | |
| 7,483,747 B2 | 1/2009 | Gliner et al. | |
| 7,588,757 B2 | 9/2009 | Ozawa et al. | |
| 7,608,245 B2 | 10/2009 | Lin | |
| 7,630,913 B2 | 12/2009 | Kay | |
| 7,658,918 B1 | 2/2010 | Ortenzi et al. | |
| 7,718,169 B2 | 5/2010 | Margolin et al. | |
| 7,736,622 B2 | 6/2010 | Lin et al. | |
| 7,935,799 B2 | 5/2011 | Lin et al. | |
| 7,945,451 B2 | 5/2011 | Cosentino et al. | |
| 8,008,036 B2 | 8/2011 | Fallon | |
| 8,012,710 B2 | 9/2011 | Fallon | |
| 8,012,930 B2 | 9/2011 | Fallon | |
| 8,030,002 B2 | 10/2011 | Fallon | |
| 8,055,516 B2 | 11/2011 | Iliff | |
| 8,066,636 B2 | 11/2011 | Iliff | |
| 8,084,025 B2 | 12/2011 | Fallon | |
| 8,105,584 B2 | 1/2012 | Fallon | |
| 8,211,661 B2 | 7/2012 | Fallon | |
| 8,221,747 B2 | 7/2012 | Ortenzi et al. | |
| 8,318,158 B2 | 11/2012 | Fallon | |
| 8,437,689 B2 | 5/2013 | Mazar | |
| 8,613,918 B2 | 12/2013 | Fallon | |
| 8,921,054 B2 | 12/2014 | Fallon | |
| 2001/0023360 A1 | 9/2001 | Nelson et al. | |
| 2001/0024660 A1 | 9/2001 | Ullah et al. | |
| 2002/0001575 A1 | 1/2002 | Foreman | |
| 2002/0037284 A1 | 3/2002 | Fallon | |
| 2002/0061302 A1 | 5/2002 | Sander-Struckmeier et al. | |
| 2002/0090653 A1 | 7/2002 | Fallon | |
| 2002/0103675 A1 | 8/2002 | Vanelli | |
| 2002/0119914 A1 | 8/2002 | Zhu et al. | |
| 2002/0141987 A1 | 10/2002 | Bjarnason | |
| 2002/0183229 A1 | 12/2002 | Simpson | |
| 2003/0097122 A1 | 5/2003 | Ganz et al. | |
| 2004/0005304 A1 | 1/2004 | Brudnak | |
| 2004/0028689 A1 | 2/2004 | Borody | |
| 2004/0029752 A1 | 2/2004 | Sava et al. | |
| 2004/0057944 A1 | 3/2004 | Galle et al. | |
| 2004/0057962 A1 | 3/2004 | Timmerman | |
| 2004/0071683 A1 | 4/2004 | Fallon | |
| 2004/0076590 A1 | 4/2004 | Wilkins | |
| 2004/0101562 A1 | 5/2004 | Maio | |
| 2004/0121002 A1 | 6/2004 | Lee et al. | |
| 2004/0209790 A1 | 10/2004 | Sava et al. | |
| 2005/0079594 A1 | 4/2005 | Marion | |
| 2005/0137134 A1 | 6/2005 | Gill et al. | |
| 2005/0170479 A1 | 8/2005 | Weaver et al. | |
| 2005/0187130 A1 | 8/2005 | Brooker et al. | |
| 2005/0232894 A1 | 10/2005 | Weiner et al. | |
| 2006/0105379 A1 | 5/2006 | Wu et al. | |
| 2006/0115467 A1 | 6/2006 | Pangborn et al. | |
| 2006/0121017 A1 | 6/2006 | Margolin et al. | |
| 2006/0182728 A1 | 8/2006 | Fallon | |
| 2006/0183180 A1 | 8/2006 | Fallon | |
| 2006/0198838 A1 | 9/2006 | Fallon | |
| 2006/0258599 A1 | 11/2006 | Childers | |
| 2006/0259995 A1 | 11/2006 | Cayouette et al. | |
| 2007/0031399 A1 | 2/2007 | Edens et al. | |
| 2007/0053895 A1 | 3/2007 | Fallon | |
| 2007/0092501 A1 | 4/2007 | Houston | |
| 2007/0116695 A1 | 5/2007 | Fallon | |
| 2007/0148151 A1 | 6/2007 | Frink et al. | |
| 2007/0148152 A1 | 6/2007 | Shlieout et al. | |
| 2007/0148153 A1 | 6/2007 | Shlieout et al. | |
| 2007/0203426 A1 | 8/2007 | Kover et al. | |
| 2008/0019959 A1 | 1/2008 | Becher et al. | |
| 2008/0020036 A1 | 1/2008 | Jolly | |
| 2008/0057086 A1 | 3/2008 | Etter | |
| 2008/0058282 A1 | 3/2008 | Fallon | |
| 2008/0112900 A1 | 5/2008 | Du-Thumm et al. | |
| 2008/0112944 A1 | 5/2008 | Pangborn et al. | |
| 2008/0152637 A1 | 6/2008 | Fallon | |
| 2008/0161265 A1 | 7/2008 | Fallon et al. | |
| 2008/0166334 A1 | 7/2008 | Fallon | |
| 2008/0254009 A1 | 10/2008 | Finegold | |
| 2008/0274174 A1 | 11/2008 | Ortenzi et al. | |
| 2008/0279839 A1 | 11/2008 | Schuler et al. | |
| 2008/0279953 A1 | 11/2008 | Ortenzi et al. | |
| 2008/0311554 A1 | 12/2008 | Slotman | |
| 2008/0317731 A1 | 12/2008 | Gramatikova et al. | |
| 2009/0117180 A1 | 5/2009 | Ortenzi et al. | |
| 2009/0226414 A1 | 9/2009 | Tijssen et al. | |
| 2009/0232789 A1 | 9/2009 | Fallon | |
| 2009/0233344 A1 | 9/2009 | Kurfurst et al. | |
| 2009/0263372 A1 | 10/2009 | Fallon | |
| 2009/0304670 A1 | 12/2009 | Edens et al. | |
| 2009/0324572 A1 | 12/2009 | Fallon | |
| 2009/0324730 A1 | 12/2009 | Fallon | |
| 2010/0092447 A1 | 4/2010 | Fallon | |
| 2010/0169409 A1 | 7/2010 | Fallon et al. | |
| 2010/0196344 A1 | 8/2010 | Margolin et al. | |
| 2010/0209507 A1 | 8/2010 | Lin et al. | |
| 2010/0233218 A1 | 9/2010 | Fallon | |
| 2010/0239559 A1 | 9/2010 | Freedman et al. | |
| 2010/0260857 A1 | 10/2010 | Fallon et al. | |
| 2010/0270183 A1 | 10/2010 | Ortenzi et al. | |
| 2010/0285116 A1 | 11/2010 | Joshi | |
| 2011/0029922 A1 | 2/2011 | Hoffberg et al. | |
| 2011/0052706 A1 | 3/2011 | Moest et al. | |
| 2011/0081320 A1 | 4/2011 | Westall et al. | |
| 2011/0112005 A1 | 5/2011 | Brooker et al. | |
| 2011/0200574 A1 | 8/2011 | Jolly et al. | |
| 2011/0280853 A1 | 11/2011 | Fallon et al. | |

(56) References Cited

U.S. PATENT DOCUMENTS

| | | |
|---|---|---|
| 2011/0280854 A1 | 11/2011 | Fallon et al. |
| 2012/0003628 A1 | 1/2012 | Fallon |
| 2012/0004192 A1 | 1/2012 | Fallon |
| 2012/0027848 A1 | 2/2012 | Fallon |
| 2012/0070504 A1 | 3/2012 | Fallon |
| 2012/0114562 A1 | 5/2012 | Fallon |
| 2012/0114626 A1 | 5/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2012/0258149 A1 | 10/2012 | Heil et al. |
| 2014/0348881 A1 | 11/2014 | Fallon |
| 2015/0023944 A1 | 1/2015 | Fallon |

FOREIGN PATENT DOCUMENTS

| | | |
|---|---|---|
| CN | 1031562 A | 3/1989 |
| CN | 1329923 A | 1/2002 |
| DE | 4332985 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1335706 B1 | 4/2005 |
| EP | 1019072 B1 | 5/2005 |
| EP | 1604677 A1 | 12/2005 |
| EP | 1931317 B1 | 6/2008 |
| EP | 2258837 A1 | 12/2010 |
| GB | 669782 A | 4/1952 |
| GB | 2347742 A | 9/2000 |
| JP | 62230714 A | 10/1987 |
| JP | H 04-364119 A | 12/1992 |
| TW | 310277 B | 7/1997 |
| WO | WO 84/02846 A1 | 8/1984 |
| WO | WO 90/02562 A1 | 3/1990 |
| WO | WO 94/19005 A1 | 9/1994 |
| WO | WO 95/22344 A1 | 8/1995 |
| WO | WO 97/32480 A1 | 9/1997 |
| WO | WO 98/22499 A2 | 5/1998 |
| WO | WO 98/22499 A3 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 00/21504 A1 | 4/2000 |
| WO | WO 01/27612 A2 | 4/2001 |
| WO | WO 01/43764 A2 | 6/2001 |
| WO | WO 01/45835 A1 | 6/2001 |
| WO | WO 01/27612 A3 | 10/2001 |
| WO | WO 01/43764 A3 | 11/2001 |
| WO | WO 02/14537 A2 | 2/2002 |
| WO | WO 02/14537 A3 | 5/2002 |
| WO | WO 02/051352 A2 | 7/2002 |
| WO | WO 03/051345 A2 | 6/2003 |
| WO | WO 03/059088 A1 | 7/2003 |
| WO | WO 2004/060074 A1 | 7/2004 |
| WO | WO 2005/115445 A1 | 12/2005 |
| WO | WO 2006/031554 A2 | 3/2006 |
| WO | WO 2006/044529 A1 | 4/2006 |
| WO | WO 2006/031554 A3 | 9/2006 |
| WO | WO 2007/002572 A2 | 1/2007 |
| WO | WO 2007/147714 A1 | 12/2007 |
| WO | WO 2008/021987 A2 | 2/2008 |
| WO | WO 2008/102264 A2 | 8/2008 |
| WO | WO 2009/114757 A2 | 9/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2010/120781 A1 | 10/2010 |
| WO | WO 2011/000924 A1 | 1/2011 |

OTHER PUBLICATIONS

U.S. Appl. No. 13/757,412, filed Feb. 1, 2013, Fallon et al.
Mitsui, et al. Role of aminopepridases in the blood pressure regulation. Biological and Pharmaceutical Bulletin of Japan, Pharmaceutical Sociey of Japan. 2004; 27(6):768-771.
Office action dated Mar. 5, 2013 for U.S. Appl. No. 12/493,122.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
USDA. FDA Drug Safety Communication: *Clostridium difficile*-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
U.S. Appl. No. 14/007,793, filed Sep. 26, 2013, Fallon.
U.S. Appl. No. 14/037,652, filed Sep. 26, 2013, Fallon.
U.S. Appl. No. 14/037,696, filed Sep. 26, 2013, Fallon.
Notice of allowance dated Oct. 29, 2013 for U.S. Appl. No. 13/204,881.
Office action dated Oct. 24, 2013 for U.S. Appl. No. 13/313,708.
Office action dated Nov. 29, 2013 for U.S. Appl. No. 13/193,346.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 16, 2013 for U.S. Appl. No. 12/535,676.
Okahata, et al. Lipid-coated enzymes as efficient catalysts in organic media. Trends in Biotechnology. 1997; 15(2):50-54.
Xu. Pancreatin therapy in chronic pancreatitis. Clin J Dig, May 2005; 25(5):313-315. (in Chinese with English translation).
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Childhood Autism Rating Scale (CARS), Wikipedia, downloaded May 5, 2014.
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Curemark press release. Curemark Receives Investigational New Drug Clearance for CM-AT for Autism. Mar. 26, 2009. http://www.medicalnewstoday.com/releases/143723.php.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Office action dated Apr. 10, 2014 for U.S. Appl. No. 13/502,989.
Office action dated Apr. 16, 2014 for U.S. Appl. No. 13/705,763.
Office action dated May 12, 2014 for U.S. Appl. No. 13/733,873.
Office action dated May 13, 2014 for U.S. Appl. No. 13/313,629.
Office action dated May 15, 2014 for U.S. Appl. No. 13/448,061.
Office action dated May 16, 2014 for U.S. Appl. No. 13/313,708.
Pancreatin 8X USP Powder. Product Specification. Jul. 2000. In: Product Manual. American Laboratories Incorporated. Omaha, NE. p. 1.
Williams, et al. Intravenous secretin for autism spectrum disorders (ASD). Cochrane Database Syst Rev. Apr. 18, 2012;4:CD003495. doi: 10.1002/14651858.CD003495.pub3.
U.S. Appl. No. 14/087,930, filed Nov. 22, 2013, Fallon et al.
Digestive Enzyme Preparation: Pancreatin listed in Japanese Pharmacopoeia, Aug. 2008, <URL:http://database.japic.or.jp/pdf/newPINS/00009938.pdf> (in Japanese with English translation).
Lebenthal, et al. Enzyme therapy for pancreatic insufficiency: present status and future needs. Pancreas. Jan. 1994;9(1):1-12.
MacDonald. Thyrotoxicosis treated with pancreatic extract and iodine. Lancet. 1943; 244(6251):788.

(56) References Cited

OTHER PUBLICATIONS

Notice of allowance dated Jan. 2, 2014 for U.S. Appl. No. 13/204,881.
Office action dated Jan. 15, 2014 for U.S. Appl. No. 13/836,135.
Office action dated Jan. 16, 2014 for U.S. Appl. No. 12/046,252.
Office action dated Jan. 24, 2014 for U.S. Appl. No. 12/054,343.
Office action dated Jan. 24, 2014 for U.S. Appl. No. 12/786,739.
Office action dated Mar. 11, 2014 for U.S. Appl. No. 11/533,818.
U.S. Appl. No. 13/926,822, filed Jun. 25, 2013, Fallon.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Carroccio, et al. Pancreatic enzyme therapy in childhood celiac disease. A double-blind prospective randomized study. Dig Dis Sci. Dec. 1995;40(12):2555-60.
Creon. Full prescribing information. Last edited Mar. 2013. Abbvie Inc 2012. www.rxabbvie.com/pdf/creon_PI.pdf.
Eaves, et al. The criterion-related validity of the Childhood Autism Rating Scale and the Autism Behavior Checklist. J Abnorm Child Psychol. Oct. 1993;21(5):481-91. abstract only.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
International search report and written opinion dated Aug. 27, 2013 for PCT/US2013/043444.
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Leeds, et al. Is exocrine pancreatic insufficiency in adult coeliac disease a cause of persisting symptoms? Aliment Pharmacol Ther. Feb. 1, 2007;25(3):265-71.
Notice of Allowance dated May 29, 2013 for U.S. Appl. No. 13/481,087.
Notice of allowance dated Aug. 19, 2013 for U.S. Appl. No. 13/208,963.
Notice of allowance dated Aug. 30, 2013 for U.S. Appl. No. 12/047,818.
Office action dated Jun. 25, 2013 for U.S. Appl. No. 13/144,286.
Office action dated Jun. 25, 2013 for U.S. Appl. No. 13/144,290.
Office action dated Jul. 15, 2013 for U.S. Appl. No. 13/002,136.
Office action dated Jul. 31, 2013 for U.S. Appl. No. 13/757,412.
Office action dated Aug. 2, 2013 for U.S. Appl. No. 12/535,676.
Office action dated Aug. 14, 2013 for U.S. Appl. No. 13/448,061.
Office action dated Aug. 28, 2013 for U.S. Appl. No. 13/313,629.
Office action dated Sep. 9, 2013 for U.S. Appl. No. 13/502,989.
Pancrease. Patient information leaflet. Pancrease HL Capsules. Last updated Apr. 30, 2013. Janssen-cilag Ltd. www.medicines.org.uk/EMC/medicine/7326.
Petrolatum: Pharmaceutical Excipients. London: Pharmaceutical Press. 2006. 1-6.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
U.S. Appl. No. 13/503,844, filed Apr. 24, 2012 Fallon et al.
U.S. Appl. No. 13/562,999, filed Jul. 31, 2012, Fallon.
U.S. Appl. No. 13/705,763, filed Dec. 5, 2012, Fallon et al.
U.S. Appl. No. 13/733,873, filed Jan. 3, 2012, Fallon et al.
ABCNews. Changing Face of Autism: Numbers Rise as More Behaviors Included. ABCnews. Nov. 1, 2007.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 20008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Ash. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.

(56) References Cited

OTHER PUBLICATIONS

Ashwood, et al. Intestinal lymphocyte populations in children with regressive autism: evidence for extensive mucosal immunopathology. J Clin Immunol. Nov. 2003;23(6):504-17.

Ashwood, et al. Spontaneous mucosal lymphocyte cytokine profiles in children with autism and gastrointestinal symptoms: mucosal immune activation and reduced counter regulatory interleukin-10. J Clin Immunol Nov. 2004;24(6):664-73.

Austic. Development and adaptation of protein digestion. J Nutr. May 1985;115(5):686-97.

Autism Diagnosis. Autism Statistics. Www.autism-diagnosis.com/autism_statistics/autism_statistics.html. 2007.

Autism Society of America. Incidence Numbers from Other Countries. www.autism-society.org. Accessed: Jul. 14, 2008.

Awazuhara, et al. Antigenicity of the proteins in soy lecithin and soy oil in soybean allergy. Clin Exp Allergy. Dec. 1998;28(12):1559-64.

Axcan Pharma Inc. Cdn Prescribing Information on VIOKASE Pancrelipase, USP tablets, powder. 2000: 1-3.

Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.

Azilect et al. "Correlation between protein intake and daily levodopa dosage," Obtained from the interne May 2, 2007, http://www.azilect.eu/media/cnsnews/showitem.aspx?i=d1c603e4-3c61-4 aa1-a3 76-6e519a5a0f80.

Bailey, et al. Co-occurring conditions associated with FMR1 gene variations: findings from a national parent survey. Am J Med Genet A. Aug. 15, 2008;146A(16):2060-9.

Bakkaloglu, et al. Atopic features in early childhood autism. Eur J Paediatr Neurol. Nov. 2008;12(6):476-9.

Barlow. A comparison of the blood pressure, kidney volume and the pancreatic secretory response following the vein administration of various secretin preparations. Am J Phys. 1927;81:182-188.

Barnhart, et al. Symptomatic granular cell tumor involving the pituitary gland in a dog: a case report and review of the literature. Vet Pathol. May 2001;38(3):332-6.

Beilmann, et al. Neoexpression of the c-met/hepatocyte growth factor-scatter factor receptor gene in activated monocytes. Blood. Dec. 1, 1997;90(11):4450-8.

Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.

Belmonte et al. Fragile X syndrome and autism at the intersection of genetic and neural networks. Nat Neurosci. Oct. 2006; 9(10):1221-5 (abstract only).

Berg, et al. Section 10.5 Many Enzymes Are Actived by Specific Proteolytic Cleavage. 2002.

Berg, et al. Section 9.1 Proteases: Facilitating a Difficult Reaction. 2002.

Berg, et al. Table of Contents. Biochemistry, 5th edition. 2002.

Birnbaum, et al. Heat shock or stress proteins and their role as autoantigens in multiple sclerosis. Ann N Y Acad Sci. Dec. 19, 1997;835:157-67. Abstract only.

Blackmer. Parkinson disease: treatment and medication. Mar. 10, 2009., retrieved from the internet on Sep. 15, 2009, http://emedicine.medscape.com/article/312519-treatment.

Blog. Acid Phosphatase Research (blog). Acid-phosphatase.blogspot.com. 2008.

Bode et al. Usefulness of a simple photometric determination of chymotrypsin activity in stools—results of a multicentre study. Clin Biochem. 1986; 19:333-37.

Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.

Borowitz, et al. Use of pancreatic enzyme supplements for patients with cystic fibrosis in the context of fibrosing colonopathy. Consensus Committee. J Pediatr. Nov. 1995;127(5):681-4.

Boyd, et al. Positively charged amino acid residues can act as topogenic determinants in membrane proteins. Proc Natl Acad Sci U S A. Dec. 1989;86(23):9446-50.

Bradstreet, et al. Detection of Measles Virus Genomic RNA in Cerebrospinal Fluid of Children with Regressive Autism: a Report of Three Cases. J. Am Phys Surg. 2004; 9(2):38-45.

Brown. Background to Parkinson's Disease. biomed.brown.edu. Jul. 14, 2008.

Brudnak et al. Enzyme-based therapy for autism spectrum disorders—is it worth another look? Med Hypoth. 2002; 58:422-428.

Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.

Calderon-Garciduenas, et al. Immunotoxicity and environment: immunodysregulation and systemic inflammation in children. Toxicol Pathol. 2009;37(2):161-9.

Campbell et al. A genetic variant that disrupts MET transcription is associated with autism. Proc Natl Acad Sci USA. 2006; 103(45):16834-16839.

Campbell, et al. Distinct genetic risk based on association of MET in families with co-occurring autism and gastrointestinal conditions. Pediatrics. Mar. 2009;123(3):1018-24.

Carlton. Autism and malnutrition: the milk connection. Retrieved from the internet on Feb. 18, 2008, http://www.mercola.com/2004/autism_malnutrition.htm.

Caronna, et al. Autism spectrum disorders: clinical and research frontiers. Arch Dis Child. Jun. 2008;93(6):518-23.

Carroccio, et al. Secondary impairment of pancreatic function as a cause of severe malabsorption in intestinal giardiasis: a case report. Am J Trop Med Hyg. Jun. 1997;56(6):599-602.

Carroccio, et al. Secretin-cerulein test and fecal chymotrypsin concentration in children with intestinal giardiasis. Int J Pancreatol. Oct. 1993;14(2):175-80.

Cassidy, et al. A new concept for the mechanism of action of chymotrypsin: the role of the low-barrier hydrogen bond. Biochemistry. Apr. 15, 1997;36(15):4576-84.

CDC. Attention-Deficit/Hyperactivity Disorder (ADHD). Www.cdc.org. 2005.

CDC. Autism Information Center/FAQs. Dept of Health and Human Services/CDC. Jan. 30, 2008.

CDC. High Blood Pressure. Division for Heart Disease Stroke Prevention. Jul. 15, 2008.

Chen, et al. Identification of two lysosomal membrane glycoproteins. J Cell Biol. Jul. 1985;101(1):85-95.

Chen, et al. Lysine 43 is trimethylated in subunit C from bovine mitochondrial ATP synthase and in storage bodies associated with batten disease. J Biol Chem. May 21, 2004;279(21):21883-7.

Cichoke, et al. The complete book of enzyme therapy. Penguin. 1998: 39, 42, 47, 50, and 53.

Claud, et a. Hypothesis: inappropriate colonization of the premature intestine can cause neonatal necrotizing enterocolitis. FASEB J. Jun. 2001;15(8):1398-403.

Cohn. Optimizing the Effectiveness of Pancreatic Enzyme Replacement Therapy (PERT). Clinical Impressions. Sep. 1, 2009; 1-4.

Concerta. ADHD Myths and Facts. ADHD Myths and Facts about medication, girls, and symptoms and causes. Concerta.net. Jul. 15, 2008.

Corring, et al. Development of digestive enzymes in the piglet from birth to 8 weeks. I. Pancreas and pancreatic enzymes. Nutr Metab. 1978;22(4):231-43.

Couet, et al. Identification of peptide and protein ligands for the caveolin-scaffolding domain. Implications for the interaction of caveolin with caveolae-associated proteins. J Biol Chem. Mar. 7, 1997;272(10):6525-33.

Coyle. Treating the Negative Symptoms of Schizophrenia: An Expert Interview with Joseph Coyle, MD. www.narsad.org/?q=node/438/latest-research. 2006.

Craig, et al. Heat shock proteins: molecular chaperones of protein biogenesis. Microbiol Rev. Jun. 1993;57(2):402-14.

Croonenberghs, et al. Peripheral markers of serotonergic and noradrenergic function in post-pubertal, caucasian males with autistic disorder. Neuropsychopharmacology. Mar. 2000;22(3):275-83.

(56) References Cited

OTHER PUBLICATIONS

Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Dajcs, et al. Lysostaphin is effective in treating methicillin-resistant *Staphylococcus aureus* endophthalmitis in the rabbit. Curr Eye Res. Jun. 2001;22(6):451-7.
Darman. An introduction to alternative medicine for psychiactric conditions. Oct. 22, 2007, retrieved on Sep. 18, 2009, http://web.archive.org/web/20071022104238/http://altp[therapie s4bipolar.info/ortho/html.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Derwent. English abstract for RU 2286785 Nov. 10, 2006. Downloaded from the Derwent file Jul. 13, 2011.
Diaz-Hernandez, et al. Neuronal induction of the immunoproteasome in Huntington's disease. J Neurosci. Dec. 17, 2003;23(37):11653-61.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between *Helicobacter pylori* infection and idiopathic parkinsonism. Medical Hypothesis. 2000; 55(2):93-98.
Dockter et al. Determination of chymotrypsin in the feces by a new photometric method. Padiatr Padol. 1985; 20(3):257-265.
Dupiereux, et al. Creutzfeldt-jakob, Parkinson, lewy body dementia and Alzheimer diseases: from diagnosis to therapy. Cent Nerv Syst Agents Med Chem. Mar. 2009;9(1):2-11.
Edelson, et al. 3-Cyclohexene-1-glycine, an Isoleucine Antagonist. J. Am. Chem. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Ethridge, et al. Acute pancreatitis results in induction of heat shock proteins 70 and 27 and heat shock factor-1. Pancreas. Oct. 2000;21(3):248-56.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Fallon. Could one of the most widely prescribed antibiotics amoxicillin/clavulanate "augmentin" be a risk factor for autism? Med Hypotheses. 2005;64(2):312-5.
Family Caregiver Alliance. Fact Sheet: Parkinson's Disease. Caregiver.org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):128-39.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of *Giardia lamblia, entamoeba histolytica/entamoeba dispar*, and *Cryptosporidium parvum* antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening Acta Paediatr. Nov. 1997;86(11):1162-5.
Goff, et al. Production of abnormal proteins in *E. coli* stimulates transcription of lon and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.

(56) References Cited

OTHER PUBLICATIONS

Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Horvath et al. Improved social and language skills after secretin administration in patients with autistic spectrum disorders. Journal of the Association for Academic Minority Physicians. Jan. 1998; 9(1):9-15.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Kearney, et al. Global burden of hypertension: analysis of worldwide data. Lancet. Jan. 15-21, 2005;365(9455):217-23. Abstract only.
Knivsberg, et al. A randomised, controlled study of dietary intervention in autistic syndromes. Nutr Neurosci. Sep. 2002;5(4):251-61.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol Jun. 2008;121(6):1455-9.
Koster et al. Evidence based medicine and extradigestive manifestations of *Helocobacter pylori*. Acta Gastro-Enterologica Belgica. 2000; 63(4):388-392.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Larimore. How Common Is ADHD? Facts About ADHD. Jul. 15, 2008.
Lashkari, et al. Williams-Beuren syndrome: An update and review for the primary physician. Clinical Pediatrics. 1999; 38(4):189-208.
Layer et al. Pancreatin enzyme replacement therapy. Current Gastroenterology Reports. 2001; 3:101-108.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
Macfabe, et al. Neurobiological effects of intraventricular propionic acid in rats: possible role of short chain fatty acids on the pathogenesis and characteristics of autism spectrum disorders. Behav Brain Res. 2006;176(1):149-69.
Macready. Parkinson's Diseasne Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-9.
Marczewska et al. Protein intake in parkinsonian using the EPIC food frequency questionnaire. Mov Diord. Aug. 2006; 21(8):1229-1231.

(56) References Cited

OTHER PUBLICATIONS

Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Janurary 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome. ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 2002 1;347(5):314-21.
Medsafe. Data sheet for alpha-lactose, Jul. 21, 1999, http://www.medsafe.govt.nz/Profs/Datasheet/a/Alphalactulosesyrup.htm.
Medscape. Burden of Hypertension in the United States Greater Than Ever. www.medscape.com. Jul. 14, 2008.
Merck. Autism, Merck manual online medical library home addition, retrieved from the interne Mar. 10, 2008, http://www.mercl.com/mmhge/sec23/ch286/ch286b.html.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michell et al. Biomarkers and parkinson's disease. Brain. 2004; 127(8):1693-1705.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56, 58, 60, 64.
Nagamoto. Jacobson: Psychiatric Secrets, 2nd ed. 2001.
Neuer, et al. The role of heat shock proteins in reproduction. Hum Reprod Update. Mar.-Apr. 2000;6(2):149-59.
Nevo et al. Acute immune polyneuropathies: correlations of serum antibodies to *Campylobacter jejuni* and *Helicobacter pylori* with anti-gm antibodies and clinical patterns of disease. J of Inf diseases. 1997; 175(S2):S154-6.
NewHorizons. ADD/ADHD: New Perspectives on Attentional Priority Disorders. New Horizons for Learning Jul. 15, 2008.
NIH. National Institutes of Health. National Diabetes Statistics 2007. diabetes.niddk.nih.gov. Jun. 1, 2008.
NINDS Dysautonimia Information Page, retrieved from the internet Sep. 10, 2009, http://www.ninds.nih.gov/disorders/dysautonomia/dysautonomia.htm.
NINDS Guillain-Barre Syndrome Information Page, retrieved from the interne Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Allowance dated Feb. 17, 2012 for U.S. Appl. No. 10/681,018.
Notice of Allowance dated Mar. 21, 2012 for U.S. Appl. No. 12/487,864.
Notice of Allowance dated Apr. 15, 2011 for U.S. Appl. No. 12/487,868.
Notice of Allowance dated Apr. 29, 2011 for U.S. Appl. No. 12/046,402.
Notice of Allowance dated May 23, 2011 for U.S. Appl. No. 09/990,909.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 8, 2011 for U.S. Appl. No. 12/046,402.
Notice of Allowance dated Aug. 8, 2011 for U.S. Appl. No. 12/426,794.
Notice of Allowance dated Sep. 20, 2011 for U.S. Appl. No. 12/283,090.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide. cmbi.bjmu.edu. Jul. 14, 2008.
Office Action dated Jan. 8, 2010 for U.S. Appl. No. 10/681,018.
Office action dated Jan. 12, 2012 for U.S. Appl. No. 12/047,818.
Office Action dated Jan. 21, 2011 for U.S. Appl. No. 12/386,051.
Office Action dated Jan. 29, 2002 for U.S. Appl. No. 09/707,395.
Office Action dated Feb. 1, 2012 for U.S. Appl. No. 12/493,122.
Office Action dated Mar. 5, 2012 for U.S. Appl. No. 12/535,676.
Office Action dated Mar. 18, 2008 for U.S. Appl. No. 11/468,379.
Office Action dated Mar. 19, 2012 for U.S. Appl. No. 13/204,881.
Office Action dated Mar. 23, 2012 for U.S. Appl. No. 13/271,783.
Office Action dated Mar. 25, 2008 for U.S. Appl. No. 11/213,382.
Office Action dated Mar. 28, 2008 for U.S. Appl. No. 11/555,697.
Office Action dated Mar. 29, 2011 for U.S. Appl. No. 12/054,343.
Office Action dated Mar. 30, 2011 for U.S. Appl. No. 12/786,739.
Office Action dated Apr. 5, 2012 for U.S. Appl. No. 11/555,697.
Office Action dated Apr. 9, 2012 for U.S. Appl. No. 13/208,963.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated Apr. 27, 2011 for U.S. Appl. No. 10/681,018.
Office Action dated Apr. 28, 2011 for U.S. Appl. No. 12/283,090.
Office Action dated May 22, 2002 for U.S. Appl. No. 09/466,559.
Office Action dated May 24, 2011 for U.S. Appl. No. 12/487,864.

(56) References Cited

OTHER PUBLICATIONS

Office action dated Jun. 13, 2012 for U.S. Appl. No. 12/493,122.
Office action dated Jun. 29, 2011 for U.S. Appl. No. 11/555,697.
Office Action dated Jun. 30, 2004 for U.S. Appl. No. 10/730,567.
Office Action dated Jul. 6, 2010 for U.S. Appl. No. 11/533,818.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Sep. 22, 2004 for U.S. Appl. No. 10/730,567.
Office Action dated Sep. 24, 2009 for U.S. Appl. No. 12/046,252.
Office Action dated Oct. 1, 2001 for U.S. Appl. No. 09/466,559.
Office Action dated Oct. 5, 2010 for U.S. Appl. No. 12/046,402.
Office action dated Oct. 19, 2011 for U.S. Appl. No. 12/386,051.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office action dated Dec. 15, 2011 for U.S. Appl. No. 12/493,147.
Office Action dated Dec. 19, 2005 for U.S. Appl. No. 10/730,567.
Office Action dated Dec. 22, 2006 for U.S. Appl. No. 10/681,018.
Owley, et al. Multisite, double-blind, placebo-controlled trial of porcine secretin in autism. J Am Acad Child Adolesc Psychiatry. Nov. 2001;40(11):1293-9.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of *Crytosporidium* oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
PDtalks. Motivational & Inspirational Speaking From a Parkinson's Patient Perspective. pdtalks.com/Parkinson_s_Disease.html. Jul. 14, 2008.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Revolution health. Enzyme therapy. revolutionhealth.com/drugs-treatments/enzyme-therapy. Sep. 2, 2008.
Rider, et al. Perspective of biochemical research in the neuronal ceroid-lipofuscinosis. Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Sahelian. Enzymes. raysahelian.com/enzymes.html. Sep. 2, 2008.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.

(56) References Cited

OTHER PUBLICATIONS

Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influecing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:I17-25.
Seneca et al. Enhancement of brain 1-dopa concetration with a-chymotrypsm. J American Geriatrics Society. 1973; 256-258.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Austim Dev Disord. 2007;38(3):546-52.
Shpacovitch, et al. Protease-activated receptors: novel PARtners in innate immunity Trends Immunol Dec. 2007;28(12):541-50.
Shpacovitch, et al. Role of protease-activated receptors in inflammatory responses, innate and adaptive immunity J Leukoc Biol. Jun. 2008;83(6):1309-22.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Skeels et al. *Crytosporidium* infection in Oregon public health clinic patients 1985-88: the value of statewide laboratory surveillance. AJPH. 1990; 80(3):305-308.
Smith, et al. Fecal chymotrypsin and trypsin determinations. Canadian Medical Association Journal. 1971; 104(8):691-4 and 697.
Statemaster. Number of Children with Autism (most recent w/graph) by state. Statemaster.com Jul. 14, 2008.
Statemaster. Number of Children with Autism (most recent) by state. Statemaster.com Jul. 14, 2008.
Statemaster. Number of Children with Autism (per capita)(most recent) by state. Statemaster.com Jul. 14, 2008.
Stein, et a. Nitrogen Metabolism in normal and hyperkinetic boys. Am J Clin Nutr. 1984; 39:520-524.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Publication Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
Tager-Flusberg, et al. Language disorders: autism and other pervasive development disorders. Pediatr Clin North Am. Jun. 2007;54(3):469-81, vi.
Terrie, et al. Understanding Pancreatic Enzyme Products. Dec. 15, 2008.
The Alzheimer's Association. Basics of Alzheimer's Disease. 2005, 32 pages. http://www.alz.org/national/documents/brochure_Basicsofalz_low/pdf.
TheFreeDictionary. Term Sprinkles Www.thefreedictionary.com. Accessed Nov. 2, 2011. 1 page.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and *Helicobacter pylori* gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010 ;57(2):149-66.
Trauner, et al. Specific cognitive deficits in young children with cystinosis: evidence for an early effect of the cystinosin gene on neural function. J Pediatr. Aug. 2007;151(2):192-6.
Tsan, et al. Heat shock proteins and immune system. J Leukoc Biol. Jun. 2009;85(6):905-10.
Tsang et al. Extragastroduodenal conditions associated with *Heliobacter pylori* infection. Hong Kong Medical Journal. 1999; 5(2):169-174.
Uhlmann, et al. Potential viral pathogenic mechanism for new variant inflammatory bowel disease. Mol Pathol. Apr. 2002;55(2):84-90.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif. students triples. United Press International. Jul. 12, 2008.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Volkmar, et al. Practice Parameters for the Assessment and Treatment of Children, Adolescents, and Adults with Autism and other Perva-

(56) References Cited

OTHER PUBLICATIONS sive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Wang, et al. Activation of Ras/Erk pathway by a novel MET-interacting protein RanBPM. J Biol Chem. Sep. 27, 2002;277(39):36216-22.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Yahoo!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zhang et al. Lactulose-mannitol intestinal permeability test in children with diarrhea caused by rotavirus abd *Cryptosporidium*. J of Pediatric Gastro & Nutrition. 2000; 31(1):16-21.
Bowers. Exocrine secretions of the pancreas. Jul. 5, 2006. Accessed online at www.vivo.colostate.edu/hbooks/pathphys/digestion/pancreas/exocrine.html.

Bray, et al. Effect of dietary protein content on weight gain, energy expenditure, and body composition during overeating. A randomized controlled trial. JAMA. Jan. 4, 2012; 307(1):47-55.
Ferrone, et al. Pancreatic enzyme pharmacotherapy. Pharmacotherapy. 2007; 27:910-920.
Information of Papain from Worthington Enzymes webpage http://www.worthington-biochem.com/pap/default.html Downloaded Jan. 17, 2013.
International search report and written opinion dated Feb. 21, 2013 for PCT/US2013/020183.
International search report and written opinion dated Nov. 12, 2012 for PCT/US2012/034489.
Notice of allowance dated Jul. 3, 2012 for U.S. Appl. No. 13/271,783.
Office action dated Jan. 22, 2013 for U.S. Appl. No. 13/562,999.
Office action dated Jan. 25, 2013 for U.S. Appl. No. 13/208,963.
Office action dated Feb. 14, 2013 for U.S. Appl. No. 13/193,346.
Office action dated Feb. 14, 2013 for U.S. Appl. No. 13/407,408.
Office action dated Feb. 21, 2013 for U.S. Appl. No. 12/047,818.
Office action dated Jun. 27, 2012 for U.S. Appl. No. 12/493,147.
Office action dated Jul. 11, 2012 for U.S. Appl. No. 12/573,353.
Office action dated Jul. 18, 2012 for U.S. Appl. No. 12/047,818.
Office action dated Aug. 13, 2012 for U.S. Appl. No. 13/208,963.
Office action dated Sep. 13, 2012 for U.S. Appl. No. 13/481,087.
Office action dated Oct. 10, 2012 for U.S. Appl. No. 13/204,881.
Office action dated Oct. 25, 2012 for U.S. Appl. No. 13/144,286.
Office action dated Oct. 25, 2012 for U.S. Appl. No. 13/144,290.
Office action dated Dec. 6, 2012 for U.S. Appl. No. 13/002,136.
Olivar-Parra, et al. Training referential communicative skills to individuals with autism spectrum disorder: a pilot study. Psychological Reports. 2011; 109:921-939.
Patel, et al. Formulation and evaluation of mucoadhesive glipizide microspheres. AAPS PharmSciTech. 2005; 6(1):E49-E55.
Serna, et al. Pathogenesis and treatment of Shiga toxin-producing *Escherichia coli* infections. Curr Opin Gastroenterol. Jan. 2008;24(1):38-47.
Tamaro. Vitamin K deficiency as a cause of autistic symptoms. Http://web.archive.org/web/20090612022246/http://www.gutre search.com/VitaminK.pdf. Published Jun. 12, 2009 as per Wayback Engine.
Walsh, et al. Reduced violent behavior following chemical therapy. Physiology and behavior. 2004; 82:835-839.
U.S. Appl. No. 13/836,135, filed Mar. 15, 2013, Fallon et al.
Chen, et al. Medicinal Functions of Bromelain and Its Application Prospect in Animal Husbandry, China Animal Husbandry & Veterinary Medicine, vol. 32, No. 1, p. 14-16. (in Chinese with English translation).
Millipore EMD catalog (online) Papain, unit definition, EMD Millipore Corp, 2013. Downloaded May 13, 2013.
Office action dated May 9, 2013 for U.S. Appl. No. 13/204,881.
Office action dated May 15, 2013 for U.S. Appl. No. 13/502,989.
Roxas, et al. Colds and influenza: a review of diagnosis and conventional, botanical, and nutritional considerations. Alternative Medicine Review. 2007; 12(1):25-48.
UK search and examination report dated Mar. 26, 2013 for GB 1111565.6.
UK search and examination report dated Mar. 27, 2013 for GB 1111566.4.
UK search and examination report dated Apr. 18, 2013 for GB 1117669.0.
Notice of allowance Aug. 11, 2014 for U.S. Appl. No. 13/193,346.
U.S. Appl. No. 14/296,091, filed Jun. 4, 2014, Fallon.
Notice of allowance dated Jun. 12, 2014 for U.S. Appl. No. 13/448,061.
Office action dated Jun. 17, 2014 for U.S. Appl. No. 13/757,412.
Office action dated Jun. 19, 2014 for U.S. Appl. No. 12/386,051.
Office action dated Jun. 27, 2014 for U.S. Appl. No. 14/007,793.
Office action dated Jul. 7, 2014 for U.S. Appl. No. 12/535,676.
U.S. Appl. No. 14/528,715, filed Oct. 30, 2014, Fallon.
U.S. Appl. No. 14/612,580, filed Feb. 3, 2015, Fallon et al.
U.S. Appl. No. 14/612,604, filed Feb. 3, 2015, Fallon et al.
U.S. Appl. No. 14/639,425, filed Mar. 5, 2015, Fallon.
U.S. Appl. No. 14/640,385, filed Mar. 6, 2015, Fallon.

(56) References Cited

OTHER PUBLICATIONS eMedExpert, Antibiotics:Cephalosporins, Available online at: www.emedexpert.com/compare/ cephalosporins.shtml, available as early as Jun. 2, 2007 per Internet Archive Wayback Machine.

GM Chemie 2010 "Products: Hypromellose Phthalate" accessed from www.gmchemie.com on Sep. 22, 2014.

Merriam-Webster 2014 "Definition: Precipitate" accessed from www.mirriam-webster.com on Sep. 22, 2014.

Munasinghe et al. Digestive enzyme supplementation for autism spectrum disorders: a double-blind randomized controlled trial. J Autism Dev Disord. Sep. 2010;40(9):1131-8.

Notice of allowance dated Feb. 2, 2015 for U.S. Appl. No. 13/926,822.

Notice of allowance dated Feb. 20, 2015 for U.S. Appl. No. 12/386,051.

Notice of allowance dated Feb. 27, 2015 for U.S. Appl. No. 14/037,696.

Notice of allowance dated Sep. 15, 2014 for U.S. Appl. No. 14/037,652.

Notice of allowance dated Dec. 23, 2014 for U.S. Appl. No. 14/007,793.

Office action dated Jan. 16, 2015 for U.S. Appl. No. 12/535,676.

Office action dated Mar. 6, 2015 for U.S. Appl. No. 13/757,412.

Office action dated Aug. 29, 2014 for U.S. Appl. No. 13/144,286.

Office action dated Sep. 18, 2014 for U.S. Appl. No. 13/502,989.

Office action dated Sep. 19, 2014 for U.S. Appl. No. 11/533,818.

Office action dated Sep. 30, 2014 for U.S. Appl. No. 13/144,290.

Office action dated Sep. 30, 2014 for U.S. Appl. No. 13/660,642.

Office action dated Oct. 2, 2014 for U.S. Appl. No. 12/054,343.

Office action dated Oct. 6, 2014 for U.S. Appl. No. 12/493,122.

Office action dated Oct. 9, 2014 for U.S. Appl. No. 12/786,739.

Office action dated Nov. 7, 2014 for U.S. Appl. No. 12/786,739.

Office action dated Nov. 21, 2014 for U.S. Appl. No. 13/926,822.

Office action dated Dec. 18, 2014 for U.S. Appl. No. 14/037,696.

Office action dated Dec. 19, 2014 for U.S. Appl. No. 13/733,873.

* cited by examiner

METHODS AND COMPOSITIONS FOR THE TREATMENT OF SYMPTOMS OF PRION DISEASES

CROSS REFERENCE TO RELATED APPLICATIONS

This application is a continuation of U.S. Utility application Ser. No. 12/573,353, filed Oct. 5, 2009, now abandoned, which claims the benefit of U.S. Provisional Application 61/102,818, filed Oct. 3, 2008, each of which is incorporated by reference in its entirety herein.

TECHNICAL FIELD

This disclosure relates to a treatment for the symptoms of prion diseases, and more particularly, to the use of pharmaceutical compositions comprising one or more digestive enzymes, such as one or more pancreatic enzymes, in the treatment of the symptoms of prion diseases. The disclosure also relates to a method of making pharmaceutical compositions comprising one or more digestive enzymes. The disclosure further relates to the use of an individual's fecal chymotrypsin level as a diagnostic marker for determining whether an individual has a prion disease, as well as to predict whether an individual will be beneficially treated with the described pharmaceutical compositions.

BACKGROUND OF THE INVENTION

Dysautonomias can result in symptoms in which one or more areas of the body are innervated by the autonomic nervous system. While some dysautonomias are well known, other conditions have yet to be determined as a dysautonomia.

Symptoms of known dysautonomias include: palpitations, chest pain, tachycardia, excessive fatigue, severe fluctuations in blood pressure, excessive sweating, fainting, exercise intolerance, shortness of breath, visual disturbances including blurred vision, tunneling, and double vision, migraines, dizziness, insomnia, gastrointestinal problems including diarrhea, and constipation, bloody stools, fainting/near fainting, frequent urination, convulsions, and cognitive impairment. Secondarily others symptoms such as depression, dysthymia, obsessive compulsive tendencies, and difficulty with ambulation and other symptoms may also be a part of the dysautonomic picture.

Conditions such as familial dysautonomia (FD), also known also as Riley-Day syndrome, Parkinson's disease, Guillaine-Barre syndrome (GBS), Dopamine-b-Hydroxalase deficiency, baroreflex failure, Guillaine-Barre Syndrome, neuroblastoma and other tumors which affect the neuroendocrine system, Aromatic L-Amino Acid Decarboxylase deficiency, Tetrahydrobiopterin deficiency, Familial Paraganglioma syndrome, "Shy-Drager Syndrome," also referred to as "Multiple System Atrophy" or MSA, Neurally Mediated Syncope, also known as Neurocardiogenic Syncope, diabetic cardiovascular neuropathy, hereditary sensory and autonomic neuropathy type III (HSAN III), Menke's disease, monoamine oxidase deficiency states, and other disorders of dopamine metabolism, dysautonomic syndromes and disorders of the cardiovasular system, Chaga's disease, diabetic autonomic failure, and pure autonomic failure, are well known as conditions associated with or primarily due to a dysautonomia.

Prion diseases are rare. The general worldwide yearly incidence is approximately one case per million people. Thus, in the US, approximately 300 de novo cases of sporadic and genetic prion disease are observed per year. The genetically transmissible forms of prion disease are about one-tenth as common as the sporadic forms. This prevalence is comparable to that observed with the autosomal dominant forms of familial Alzheimer disease and amyotrophic lateral sclerosis (Lou Gehrig's disease).

Prion diseases generally manifest with cognitive difficulties, ataxia, and myoclonus (abrupt jerking movements of muscle groups and/or entire limbs); however, the order and/or predominance of these features and associated neurologic and psychiatric findings vary with prion disease subtype and/or PRNP mutation. The age at onset ranges from the third to ninth decade of life. The course ranges from a few months to several years (typically five to seven years, but in rare cases more than ten years). Death generally results from infection, either by pneumonia (typically from aspiration) or urosepsis. Therapy is aimed at controlling symptoms that may cause discomfort. No cure for prion disease currently exists.

The three phenotypes classically associated with genetic prion disease (fCJD, GSS, and FFI), were defined by clinical and neuropathologic findings long before the molecular basis of this group of disorders was discovered. Although it is now recognized that these three phenotypes are part of a continuum and have overlapping features, it can be helpful to think of genetic human prion disease at least in part in terms of these phenotypes when providing individuals and families with information about the expected clinical course.

Familial Creutzfeldt-Jakob disease (fCJD).

Progressive confusion and memory impairment occur first, followed by ataxia and myoclonus. The disease typically manifests between the ages of 30 and 50 years, although a few individuals present before age 30 or as late as the upper 80s. The course from onset to death ranges from a few months to five years. At the endstage of disease, the individual is generally bedbound, mute, and immobile, except for myoclonic jerks.

The cognitive impairment observed may initially be mild confusion or it may be specific for a particular cortical function, such as language or constructional abilities; however, the resultant picture is one of global dementia. As the disease progresses, neurobehavioral symptoms may vary considerably. Psychiatric features, including delusions and hallucinations, may also occur.

Ataxia may be either truncal or appendicular, manifesting either as an unsteady gait, clumsiness while carrying out commonly performed tasks (e.g., picking up the salt shaker while dining), or progressive dysarthria. As the ataxia progresses, the individual may fall repeatedly, necessitating the use of a wheelchair to prevent injury.

Myoclonus generally, but not always, occurs after cognitive impairment is evident. Myoclonus may begin focally in a single limb but eventually becomes generalized. "Startle myoclonus" may be elicited by simple acts such as clapping the hands or turning on the room lights. Even if warned of an impending noise, the individual cannot suppress the startle response.

Other neurologic signs and symptoms such as focal or generalized weakness, rigidity, bradykinesia, tremor, chorea, alien hand syndrome, stroke-like symptoms, visual disturbances, and seizures have been observed.

Gerstmann-Sträussler-Scheinker syndrome (GSS).

GSS typically begins in the fourth to sixth decade with the insidious onset of cerebellar dysfunction, manifest as unsteady gait and mild dysarthria. Cognitive dysfunction is generally not apparent early on; however, with progression, bradyphrenia, or slowness of thought processing, may become evident. Pyramidal involvement with spasticity and/or extrapyramidal involvement with bradykinesia, increased muscle tone with or without cogwheeling, and masked facies are also common. Psychiatric or behavioral symptoms are atypical. The disease progresses at a relatively slow but relentless pace over the course of a few to seven or more years. Cerebellar dysfunction results in severe dysarthria, gait and appendicular ataxia, ocular dysmetria, and lack of coordination in swallowing. A decline in cognitive abilities, particularly of concentration and focus, becomes apparent with progression into the late stage of disease. In the terminal stage, the individual is bedridden from the disabling ataxia, unable to eat because of severe lack of coordination in swallowing, and unable to communicate because of the profound dysarthria; yet insight into his/her condition may remain. This pattern of progression relates to the cerebellar nature of this disease, with progression into the brain stem and eventually the cerebrum.

Fatal Familial Insomnia (FFI).

FFI typically presents in midlife (40s to 50s) with the insidious or subacute onset of insomnia, initially manifest as a mild, then more severe, reduction in overall sleep time. When sleep is achieved, vivid dreams are common. A disturbance in autonomic function then emerges, which may manifest as elevated blood pressure, episodic hyperventilation, excessive lacrimation, sexual and urinary tract dysfunction, and/or a change in basal body temperature. Signs of brainstem involvement, such as decreased ability to gaze upward, double vision, jerky eye pursuit movements, or dysarthric speech may also appear in some individuals. With continued progression over the next few months, individuals develop truncal and/or appendicular ataxia. The speed of thought processing may be reduced, as is common in subcortical dementing states, and memory impairment may be variable; however, compared with other more prominent features of disease, cognitive capacity is relatively spared until late in the course. Advancing disease results in progressively greater loss of total sleep time, worsening ataxia, and more profound confusion, leading ultimately to an awake but stuporous state as death approaches. As with other forms of prion disease, debilitation leading to feeding difficulties and loss of airway protection is the most common immediate cause of death. The typical duration of disease is 12 to 16 months, with a range of a few months to five years.

Other Prion Diseases.

About 10-15% of prion diseases are genetically transmissible, while the remainder occur from unknown risk factors or are acquired through infection with prions; these include sporadic Creutzfeldt-Jakob disease (sCJD), iatrogenic CJD (iCJD), variant CJD (vCJD), and sporadic fatal insomnia (sFI). Kuru, a prion disease associated with the practice of cannibalism in a primitive culture in New Guinea, is primarily of historical significance.

sCJD.

The clinical and pathologic features of sCJD are the same as fCJD; however, the duration of disease is typically much shorter, on the average of six months or less, and the age at onset is later, typically after age 60 years.

sFI.

The phenotype is the same as in FFI, including age at onset and duration of disease. sFI is much less common than FFI.

iCJD.

Diagnosis of this form of prion disease requires the identification or strong association with administration of a biological extract or tissue contaminated with prions. Such sources have included injections of human growth hormone contaminated with prions (used prior to 1980), improperly decontaminated depth electrodes previously used in individuals with CJD, transplantation of corneas obtained from individuals with CJD, dura mater grafts contaminated with prions, and various poorly documented neurosurgical procedures.

vCJD.

This prion disease represents a relatively new strain of CJD acquired by ingestion of beef or beef products contaminated with bovine spongiform encephalopathy (BSE), the prion disease of cattle (commonly known as mad cow disease). The typical clinical picture is that of a young adult or teen who develops behavioral changes and/or pain in the lower extremities that eventually lead to a progressive dementia with ataxia and myoclonus. The course is about 1.5 years. The EEG is often diffusively slow rather than periodic, and the 14-3-3 CSF protein test is more often negative than positive. Neuropathology reveals spongiform change spread diffusely throughout the brain and dense amyloid plaque deposition surrounded by a halo of vacuolation described as "florid plaques.

SUMMARY

It has been determined by the present inventor that the gastrointestinal tract of dysautonomic individuals is impaired, and that the proper levels of pancreatic enzymes and/or their precursors including the zymogens and bicarbonate ions are not present in sufficient quantities to allow proper digestion. While that impairment is relevant to the digestion of carbohydrates, fats and proteins, it is most specific and most severe with respect to protein digestion. Accordingly, while not being bound by theory, the present inventor believes that many, if not all, dysautonomias have a GI component, and thus that dysautonomias may actually have their etiology in gastrointestinal dysfunction. For example, with Guillaine-Barre syndrome, it is postulated that a GI pathogen is a causative factor in the formation of the Guillaine Barre dysautonomia. Similarly, it has been found by the present inventor that populations of autistic children suffer from GI disturbances and other conditions which are dysautonomic in nature. In general, these findings represent a possible link between the etiology of autism and autonomic dysfunction. Thus, the inventor believes that other dysautonomic conditions also have GI primary etiologies.

The symptoms of dysautonomic conditions, however, may have various manifestations due to the genetic makeup of the individuals suffering from the conditions. Various gene sequences in the genetic code of the individual will result in manifestation of certain diseases or symptoms that are expressed uniquely in each individual. For example, if amino acid pool deficits due to improper protein digestion and gastrointestinal dysfunction are manifested differently in different individuals, a "disease state" may appear different depending upon the genetic makeup of the individual. Neurological expression may be all that is seen in some individuals, whereas other manifestations may demonstrate a hybrid of gastrointestinal dysfunction as well as neurological or other dysfunctions.

Accordingly, while not bound by theory, the present inventor believes that prion diseases may have a dysautonomic component and that the etiology of prion diseases may be related to gastrointestinal dysfunction.

Given the above, it is a goal of the present disclosure to provide therapeutic methods and pharmaceutical compositions for the treatment of the symptoms of prion diseases. It is also a goal of the present disclosure to provide therapeutic methods and pharmaceutical compositions for the treatment of Pervasive Development Disorders such as Autism, ADD, and ADHD, and for dysautonomias such as Familial Dysautonomia, Parkinson's, and Guillaine Barre Syndrome.

Another goal of the present disclosure is the provision of pharmaceutical compositions for the treatment of the above disorders, wherein the compositions comprise one or more digestive enzymes, e.g., one or more enzymes selected from amylases, proteases, cellulases, papaya, papain, bromelain, lipases, chymotrypsin, trypsin, and hydrolases. In some embodiments, the pharmaceutical compositions are lipid encapsulated.

Yet another goal of the present disclosure is to provide methods for making the described pharmaceutical compositions using methods such as: direct compression, microencapsulation, lipid encapsulation, wet granulation or other methods including the use of Prosolv® (silicified microcrystalline cellulose), and other known excipients and additives to accomplish microencapsulation, lipid encapsulation, direct compression, wet or dry granulation or other suitable technology.

A further goal of the present disclosure is to provide means to deliver the pharmaceutical compositions, which can include the use of rapid dissolution (rapid dissolve), time release, or other delivery methods including oral, injection, patch, or other method. Further, the delivery of the pharmaceutical compositions may be in the form of a tablet, capsule, sprinkles, sachet, or other oral delivery method.

An additional goal of the disclosure is to demonstrate the use of fecal chymotrypsin level as a biomarker for the presence of prion diseases, or the likelihood of an individual to develop prion diseases.

Accordingly, provided herein is a method for treating one or more symptoms associated with prion diseases in a patient diagnosed with a prion disease comprising administering to the patient a therapeutically effective amount of a pharmaceutical composition comprising one or more digestive enzymes. In some embodiments, the pharmaceutical composition may be lipid-encapsulated. In some embodiments, the one or more digestive enzymes comprise one or more enzymes selected from the group consisting of proteases, amylases, celluloses, sucrases, maltases, papaya, papain, bromelain, hydrolases, and lipases. In some embodiments, the one or more digestive enzymes comprise one or more pancreatic enzymes. In some embodiments, the pharmaceutical composition comprises one or more proteases, one or more lipases, and one or more amylases. In some embodiments, the one or more proteases comprise chymotrypin and trypsin.

The one or more digestive enzymes are, independently, derived from an animal source, a microbial source, or a plant source, or are synthetically prepared. In some embodiments, the animal source is a pig, e.g., a pig pancreas.

In some embodiments, the pharmaceutical composition comprises at least one amylase, a mixture of proteases comprising chymotrypsin and trypsin, at least one lipase, and papain. In some embodiments, the pharmaceutical composition further comprises papaya. In some embodiments, the pharmaceutical composition comprises, per dose: amylases from about 10,000 to about 60,000 U.S.P; proteases from about 10,000 to about 70,000 U.S.P; lipases from about 4,000 to about 30,000 U.S.P; chymotrypsin from about 2 to about 5 mg; trypsin from about 60 to about 100 mg; papain from about 3,000 to about 10,000 USP units; and papaya from about 30 to about 60 mg.

In some embodiments, the pharmaceutical composition comprises at least one protease and at least one lipase, wherein the ratio of total proteases to total lipases (in USP units) ranges from about 1:1 to about 20:1. In some embodiments, the ratio of proteases to lipases ranges from about 4:1 to about 10:1.

In some embodiments, the one or more symptoms of prion diseases are selected from personality changes, psychiatric problems such as depression, lack of coordination, and/or an unsteady gait. Patients also may experience involuntary jerking movements called myoclonus, unusual sensations, insomnia, confusion, or memory problems. In the later stages of the disease, patients have severe mental impairment and lose the ability to move or speak.

In some embodiments, the pharmaceutical composition is a dosage formulation selected from the group consisting of: pills, tablets, capsules, microcapsules, mini-capsules, time released capsules, mini-tabs, sprinkles, and a combination thereof.

Also provided is a method of diagnosing a patient comprising: obtaining a fecal sample from the patient; determining a level of chymotrypsin present in the fecal sample, wherein the determination is performed at 30° C.; and diagnosing the patient as having a prion disease if the determined fecal chymotrypsin level is 8.4 U/gram or less and the patient exhibits at least one symptom associated with a prion disease. In some embodiments, the fecal chymotrypsin level is between 8.4 and 4.2 U/gram. In some embodiments, the fecal chymotrypsin level is less than 4.2 U/gram. In some embodiments, the level of chymotrypsin present in the fecal sample is determined using an enzymatic photospectrometry method. In some embodiments, the method further comprises administering to the patient an effective amount of a pharmaceutical composition comprising one or more digestive enzymes if the patient is diagnosed as having a prion disease. In some embodiments, the method further comprises determining if the administration of the pharmaceutical composition reduces or ameliorates one or more symptoms associated with a prion disease.

Also provided is a method of identifying a patient likely to benefit from administration of a pharmaceutical composition comprising one or more digestive enzymes comprising: obtaining a fecal sample from the patient; determining a level of chymotrypsin present in the fecal sample, wherein the determination is performed at 30° C.; and identifying the patient as likely to benefit from administration of the pharmaceutical composition if the determined fecal chymotrypsin level is 8.4 U/gram or less and the patient is diagnosed with a prion disease. In some embodiments, the method further comprises determining if the patient exhibits one or more symptoms of a prion disease. In some embodiments, the benefit comprises a reduction or amelioration of one or more symptoms associated with a prion disease. In some embodiments, the method further comprises administering to the patient an effective amount of a pharmaceutical composition comprising one or more digestive enzymes.

Also provided is a pharmaceutical composition comprising one or more digestive enzymes, wherein the one or more digestive enzymes comprise at least one lipase and at least one protease, and wherein the ratio of total proteases to total lipases (in USP units) ranges from about 1:1 to about 20:1. In some embodiments, the ratio of total proteases to total lipases ranges from about 4:1 to about 10:1. In some embodiments, the pharmaceutical composition is lipid encapsulated.

Also provided is a pharmaceutical composition comprising at least one amylase, a mixture of proteases comprising chymotrypsin and trypsin, at least one lipase, and papain. In some embodiments, the pharmaceutical composition further comprises papaya. In some embodiments, the ratio of total proteases to total lipases ranges from about 1:1 to about 20:1.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

The present disclosure provides pharmaceutical compositions and methods for treating symptoms associated with CRPS, Pervasive Development Disorders, and Dysautonomias. The pharmaceutical compositions described herein include one or more digestive enzymes, which are postulated by the present inventor to assist in proper digest protein and thus to ameliorate the gastrointestinal dysfunction that is associated with the described disorders.

In certain embodiments, the pharmaceutical compositions may include one or more digestive enzymes, wherein the one or more digestive enzymes comprise at least one lipase and at least one protease, and wherein the ratio of total proteases to total lipases (in USP units) ranges from about 1:1 to about 20:1. In some cases, the ratio of total proteases to total lipases ranges from about 4:1 to about 10:1.

In some cases, a pharmaceutical composition for use herein comprises at least one amylase, at least one protease, and at least one lipase. In certain embodiments, the pharmaceutical composition includes multiple proteases, including, without limitation, chymotrypsin and trypsin. In certain embodiments, the composition can further include one or more hydrolases, papain, bromelain, papaya, celluloses, pancreatin, sucrases, and maltases.

The one or more enzymes can be independently derived from animal, plant, microbial, or synthetic sources. In some embodiments, the one or more enzymes are derived from pig, e.g.: pig pancreas.

One exemplary formulation for the treatment of the symptoms of prion diseases is as follows:
Amylase 10,000-60,000 U.S.P
Protease 10,000-70,000 U.S.P
Lipase 4,000-30,000 U.S.P
Chymotrypsin 2-5 mg
Trypsin 60-100 mg
Papain 3,000-10,000 USP units/mg
Papaya 30-60 mg Additional formulations comprising one or more digestive enzymes may be advantageous including formulations in which the ratio of total proteases to total lipases (in USP units) is from about 1:1 to about 20:1. In some embodiments, the ratio of total proteases to total lipases is from about 4:1 to about 10:1. Such formulations are useful for treating symptoms of prion diseases as well as dysautonomias (e.g., familial dysautonomia, Parkinson's, Guillaine-Barre Syndrome, Aromatic-L-amino acid decarboxylase deficiency, tetrahydrobiopterin deficiency, familial paranganglioma syndrome; multiple system atrophy, dysautonomic symptoms associated with tumors such as pheochromocytoma, chemodectoma, and neuroblastoma; neurally mediated syncope, and SIDS) and pervasive development disorders such as autism, ADHD, ADD, and Asperger's.

Patients below the age of 18 are typically given a dosage such that the formulation would deliver at least 5,000 USP units of protease and no more than 10,000 USP units of lipase per kilogram weight of patient, per day. Beneficially, the formulation would deliver at least 5,000 USP units of protease and no more than 7,500 USP units of lipase per kilogram weight of patient per day. Patients above the age of 18 are typically given no less than 5,000 USP units of protease per kilogram weight of patient per day.

The dosage formulation may be administered by an oral preparation including, but not limited to, an encapsulated tablet, mini-tabs, microcapsule, mini-capsule, time released capsule, sprinkle or other methodology. In one embodiment, the oral preparation is encapsulated using lipid. Alternatively, the oral preparation may be encapsulated using enteric coating or organic polymers. A formulation may also be prepared using Prosolv® technology, direct compression, dry granulation, wet granulation, and/or a combination of these methods.

Fecal chymotrypsin level is a sensitive, specific measure of proteolytic activity, see e.g.: U.S. Pat. No. 6,660,831, incorporated by reference herein. Normal levels of chymotrypsin are considered be greater than 8.4 U/gram. Decreased values (less than 4.2 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

For the fecal chymotrypsin test, a stool sample is collected from each of the subjects. Each stool sample can be analyzed using an enzymatic photo spectrometry analysis to determine the level of fecal chymotrypsin in the stool; in some cases the assay is performed at 30° C., see e.g.: U.S. Pat. No. 6,660,831, incorporated by reference herein. Alternatively, other methods, such as the colorimetric method, use of substrates, use of assays, and/or any other suitable method may be used to measure the fecal chymotrypsin levels. The levels of fecal chymotrypsin in the samples of the individuals having a prion disease are compared to the levels of fecal chymotrypsin in individuals not diagnosed with a prion disease determine if the individuals having the prion disease would benefit from the administration of digestive enzymes.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for treating one or more symptoms of a prion disease in a patient diagnosed with the prion disease, the method comprising administering to the patient a therapeutically effective amount of a pharmaceutical composition consisting essentially of a mixture of digestive enzymes the mixture comprising at least a protease, an amylase, and a lipase, whereby one or more symptoms of the prion disease is treated; wherein said patient diagnosed with the prion disease has a subnormal level of fecal chymotrypsin.

2. The method of claim 1, wherein the digestive enzymes further comprise one or more enzymes selected from the group consisting of a cellulase, a sucrase, and a maltase.

3. The method of claim 1, wherein the digestive enzymes are pancreatic enzymes.

4. The method of claim 1, wherein the protease is chymotrypsin or trypsin.

5. The method of claim 1, wherein the digestive enzymes are, independently, derived from an animal source, a microbial source, or a plant source, or are synthetically prepared.

6. The method of claim 1, wherein the pharmaceutical composition comprises amylase in an amount of from about 10,000 to about 60,000 United States Pharmacopeia (U.S.P) units per dose.

7. The method of claim 1, wherein the protease and lipase in the pharmaceutical composition (in U.S.P. units) are present in a ratio of from about 1:1 to about 20:1.

8. The method of claim 7, wherein the ratio of protease to lipase is from about 4:1 to about 10:1.

9. The method of claim 1, wherein the patient exhibits one or more symptoms selected from the group consisting of personality changes, psychiatric problems, lack of coordination, unsteady gait, myoclonus, unusual sensations, insomnia, confusion, memory problems, severe mental impairment, loss of the ability to move or speak, and a combination thereof.

10. The method of claim 1, wherein the pharmaceutical composition is a dosage formulation selected from the group consisting of: a pill, a tablet, a capsule, a microcapsule, a mini-capsule, a time released capsule, a mini-tab, a sprinkle, and a combination thereof.

11. The method of claim 1, wherein the subnormal level of fecal chymotrypsin level is 8.4 U/gram or less.

12. The method of claim 1, wherein the pharmaceutical composition comprises protease in an amount of from about 10,000 to about 70,000 U.S.P units per dose.

13. The method of claim 1, wherein the pharmaceutical composition comprises lipase in an amount of from about 4,000 to about 30,000 U.S.P units per dose.

14. The method of claim 4, wherein the pharmaceutical composition comprises chymotrypsin in an amount of from about 2 to about 5 mg per dose.

15. The method of claim 4, wherein the pharmaceutical composition comprises trypsin in an amount of from about 60 to about 100 mg per dose.

* * * * *